US011993795B2

United States Patent
Jiang et al.

(10) Patent No.: US 11,993,795 B2
(45) Date of Patent: May 28, 2024

(54) ALGINATE LYASE AND APPLICATION THEREOF

(71) Applicant: Jiangnan University, Wuxi (CN)

(72) Inventors: Bo Jiang, Wuxi (CN); Tao Zhang, Wuxi (CN); Qing Meng, Wuxi (CN); Jingjing Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 391 days.

(21) Appl. No.: 17/463,628

(22) Filed: Sep. 1, 2021

(65) Prior Publication Data

US 2021/0403894 A1 Dec. 30, 2021

Related U.S. Application Data

(63) Continuation of application No. PCT/CN2020/101029, filed on Jul. 9, 2020.

(30) Foreign Application Priority Data

Jul. 24, 2019 (CN) .......................... 201910671324.0
Jul. 24, 2019 (CN) .......................... 201910671672.8
Jul. 24, 2019 (CN) .......................... 201910672205.7

(51) Int. Cl.
*C12N 9/88* (2006.01)
*C12N 1/20* (2006.01)
*C12R 1/19* (2006.01)

(52) U.S. Cl.
CPC .............. *C12N 9/88* (2013.01); *C12N 1/205* (2021.05); *C12R 2001/19* (2021.05); *C12Y 402/02003* (2013.01)

(58) Field of Classification Search
CPC ........ C12N 9/88; C12N 1/20; C12R 2001/19; C12Y 402/02
See application file for complete search history.

(56) References Cited

U.S. PATENT DOCUMENTS

2011/0236938 A1 * 9/2011 Yoshikuni ............... C12P 17/10
435/146

FOREIGN PATENT DOCUMENTS

| CN | 110257410 A | 9/2019 |
| CN | 110272852 A | 9/2019 |
| CN | 110331122 A | 10/2019 |
| CN | 110438111 A | 11/2019 |
| WO | 2018039639 A1 | 3/2018 |

OTHER PUBLICATIONS

Sun et al. Protein Expression and Purification, 2019, 153, 97-104 (Year: 2019).*
Jiang et al. Protein Expression and Purification, 2019, 161, 17-27 (Year: 2019).*
"Alginate lyase[Vibrio penaeicida] NCBI Reference Sequence:WP_126606635.1", NCBI GenPept,Dec. 28, 2018.
Zhuang J.J. et. al, "Characterization of a Novel PolyM-Preferred Alginate Lyase from Marine Vibrio splendidus OU02", Mar. Drugs,vol. 16, Issue 295, Aug. 22, 2018.
Xu Chao et. al., "Screening and Identification of a Marine Alginate-degrading Bacteriumand the Utilization Capacity of Polysaccharide" Biotechnology Bulletin, 2017, 33 (4): 198-204.
Gao, Jie el. al., "Cloning and expression of alginate lyase genes from Vibrio alginolyticus and characterization of thealginate lyase." Chin J Biotech, 2018, 34(7): 1178 1188.
Li, Yuntao et. al. "Screening of alginate lyase producing microorganisms and optimizationof fermentation conditions in disc abalone" J. Dalian Ocean University vol. 32 No. 5, Oct. 2017.

* cited by examiner

*Primary Examiner* — Lianko G Garyu
*Assistant Examiner* — Lioubov G Korotchkina
(74) *Attorney, Agent, or Firm* — IPRO, PLLC (57) ABSTRACT

The disclosure discloses an alginate lyase and application thereof, and belongs to the technical field of biology. The alginate lyase provided by the disclosure has high degradation activity, and the enzyme activity reaches 65 U/mg; the alginate lyase is stable in nature, and the enzyme activity remains 98% or higher of the initial enzyme activity after storage at 4° C. for 18 months; and the alginate lyase has high product specificity. The disclosure uses *E. coli* as a host to express the alginate lyase derived from *V. natriegens*, the obtained recombinant *E. coli* can produce the alginate lyase secreted extracellularly in a conventional LB medium without adding an induction substrate sodium alginate, so the downstream processing technology of protein is simplified, and the disclosure has great industrial application potential.

13 Claims, 6 Drawing Sheets

Specification includes a Sequence Listing.

SEQUENCE LISTING

```
<160> NUMBER OF SEQ ID NOS: 6

<210> SEQ ID NO 1
<211> LENGTH: 521
<212> TYPE: PRT
<213> ORGANISM: Vibrio natriegens

<400> SEQUENCE: 1

Met Lys His Ile Phe Phe Lys Ser Leu Leu Ala Ser Ser Ile Leu Leu
1               5                   10                  15

Ala Val Gly Cys Asn Ser Thr Ala Thr Ala Lys Ala Asp Phe Pro Asn
            20                  25                  30

Asn Gln Glu Thr Gly Val Asp Ile Leu Thr Pro Val Ala Ile Thr Ala
        35                  40                  45

Ser Ser His Asp Gly Asn Val Pro Glu Asn Leu Leu Asp Gln Asp Ile
    50                  55                  60

Met Thr Arg Trp Ala Ala Asn Gly Asp Gly Glu Trp Ala Met Leu Asp
65                  70                  75                  80

Tyr Gly Ser Val Tyr Gly Phe Asp Ala Ile Gln Ala Ser Phe Ser Lys
                85                  90                  95

Gly Asn Glu Arg Val Thr Ser Phe Asp Val Gln Phe Ser Thr Asp Gly
            100                 105                 110

Glu Asn Trp Val Thr Val Ile Glu Gly Ala Gln Ser Ser Gly Arg Ala
        115                 120                 125

Leu Gly Leu Glu Arg Phe Gln Phe Glu Pro Ala Val Lys Ala Arg Tyr
    130                 135                 140

Val Arg Tyr Val Gly His Gly Asn Thr Lys Asn Gln Trp Asn Ala Val
145                 150                 155                 160

Thr Glu Met Ala Ala Val Asn Cys Gly Ile Asn Ala Cys Pro Ala Ser
                165                 170                 175

His Val Ile Thr Asp Asp Val Val Lys Ala Glu Ala Thr Met Ile Ala
            180                 185                 190

Ala Met Lys Ala Lys Glu Lys Ala Gln Lys Glu Leu Leu Lys Asn Asn
        195                 200                 205

Arg Lys Gly Asp Phe Gly Glu Pro Ile Val Arg Pro Cys Gly Thr Thr
    210                 215                 220

Val Thr Cys Asp Leu Thr Lys Ala Met Pro Ser Pro Thr Leu Pro Ala
225                 230                 235                 240

Val Pro Leu Ala Lys Asn Ala Pro Gly Gln Asn Phe Asp Leu Thr Arg
                245                 250                 255

Trp Lys Leu Thr Thr Pro Phe Asp His Asp Lys Asp Gly Arg Ala Asp
            260                 265                 270

Asp Ile Asp Glu Trp Asp Met Ala Asn Gly Phe Gln His Pro Asp Ile
        275                 280                 285

Phe Tyr Thr Ala Asp Asp Gly Gly Met Val Phe Lys Ser Tyr Val Lys
```

```
                  290                 295                 300
Gly Ala Arg Thr Ser Lys Asn Thr Lys Tyr Ala Arg Thr Glu Leu Arg
305                 310                 315                 320

Thr Met Leu Arg Ala Gly Glu Lys Ser His Ser Thr Lys Gly Val Asn
                325                 330                 335

Pro Asn Asn Trp Val Phe Ser Ser Ala Pro Val Glu Asp Gln Lys Ala
                340                 345                 350

Ala Gly Gly Val Asp Gly Thr Leu Glu Ala Thr Leu Lys Ile Asp His
            355                 360                 365

Ala Thr Thr Thr Gly Gln Ser His Glu Val Gly Arg Phe Ile Ile Gly
370                 375                 380

Gln Ile His Asp Lys Asp Asp Glu Pro Ile Arg Leu Tyr Tyr Arg Lys
385                 390                 395                 400

Leu Pro Asp Gln Pro Thr Gly Thr Val Tyr Phe Ala His Glu Lys Thr
                405                 410                 415

Lys Thr Gly Thr Glu Asp Tyr Tyr Ser Leu Val Gly Asp Met Thr Gly
                420                 425                 430

Glu Ile Gly Asn Asp Gly Ile Ala Leu Gly Glu Lys Phe Ser Tyr Ile
            435                 440                 445

Ile Asp Val Lys Gly Asn Thr Met Thr Val Thr Val Lys Arg Asp Gly
            450                 455                 460

Lys Asp Asp Val Val Gln Val Val Asp Met Ser Asp Ser Gly Tyr Asp
465                 470                 475                 480

Glu Gly Gly Arg Tyr Met Tyr Phe Lys Ala Gly Val Tyr Asn Gln Asn
                485                 490                 495

Met Tyr Gly Asn Pro Asp Asp Tyr Ala Gln Ala Thr Phe Tyr Lys Leu
                500                 505                 510

Asp Gln Ser Phe Gly Lys Tyr Gln Gly
            515                 520

<210> SEQ ID NO 2
<211> LENGTH: 1566
<212> TYPE: DNA
<213> ORGANISM: Vibrio natriegens

<400> SEQUENCE: 2
atgaagcata ttttcttcaa aagcttgtta gcttcttcaa tcctattggc tgttggttgt      60
aacagcactg caactgcgaa ggctgatttc ccaaacaatc aagaaaccgg cgttgacatt     120
ctaactcctg ttgcaatcac ggcgagtagc catgatggta atgtgcctga gaacttactt     180
gaccaagata ttatgactcg ctgggcagcg aacggtgacg gtgagtgggc aatgttggat     240
tacggctcag tttatgggtt cgatgcaatc caagcgtcgt ttagtaaagg taatgaacgt     300
gtcacgtcat tgatgttcag ttcagcaca gatggtgaaa actgggtaac ggttattgaa     360
ggtgcacaaa gctctggtcg tgctcttggt ctggaacgct tccagttcga gcctgcggta     420
aaagctcgtt atgtacgtta cgttggccac ggcaatacca aaaaccaatg gaacgctgtt     480
actgaaatgg ccgcggttaa ctgtggaatc aatgcgtgcc cggcaagcca tgtcattacc     540
gatgatgttg ttaaagctga agcgactatg attgctgcaa tgaaggctaa ggaaaaagcg     600
caaaaggaac tccttaaaaa taatcgcaaa ggtgatttcg agaaccaat cgtccgtcct     660 tgcgggacga cagtgacgtg tgacctaact aaagcaatgc catccccaac gctaccggct     720
gttccactag ctaagaatgc accaggccaa aactttgacc tgacgcgctg aaactgaca     780 acgcctttcg atcacgacaa agacggccgc gctgatgata ttgatgagtg ggatatggca     840
```

```
aacggcttcc agcacccaga tatcttctac acagctgatg atggcggcat ggttttcaag    900
agctatgtaa aaggtgcacg tacctctaaa aatactaagt acgcacgtac agagttgcgc    960
actatgctgc gtgcgggtga gaagtctcac agtacaaaag gtgtaaatcc aaataactgg   1020
gtattcagct cagcgccggt agaagatcag aaagcagcgg gtggggtaga tggcacgctt   1080
gaggcaactc tgaagattga ccatgcaacc acaacgggtc agtcacacga agttggccgt   1140
ttcattatcg gtcagattca tgacaaagat gatgagccaa ttcgccttta ctaccgtaag   1200
ctaccagacc agccaacagg tacggtttac ttcgctcacg aaaaaaccaa aacaggtact   1260
gaagattact acagcctggt tggtgatatg actggtgaaa tcggtaacga tggtatcgcg   1320
ctaggtgaaa aattcagcta catcattgat gtaaaaggca acacgatgac agttacggta   1380
aaacgtgacg gtaaagatga tgttgtacaa gtcgtagata tgagtgacag tggttatgat   1440
gagggtggcc gatacatgta cttcaaggcc ggtgtttata accagaatat gtacggcaat   1500
ccagatgatt acgctcaagc aactttctac aagctagatc aatcttttgg taagtaccaa   1560
ggctag                                                              1566

<210> SEQ ID NO 3
<211> LENGTH: 2082
<212> TYPE: DNA
<213> ORGANISM: Vibrio natriegens

<400> SEQUENCE: 3
atgagcaacc aaaagtctct tgacgctatt agaaagataa agctggagaa tgatacatca     60
gctggaaacc ttgttgactt attgcctatc gaagtacaaa aacgcgactt cgatctgtca    120
tttctagata ccttgagtga agctcgtcca cgcctgctag tccaagctga gcagcttgaa    180
gaattcaaag cgaaagtaca ggctgatgag tcttactgta tgttcgacga tttctacaat    240
aactcgacgg ttaagtttct tgaaactgaa ccttatgaag agccaagcc ttacccggaa    300 gagacagttg gaaaagcttc tctatggcgt ccttactggc gtcaaatgta tgttgattgc    360
cagatggcgc ttaacgcgac acgtaacttg gctattgccg gaatcgttaa agaagatgaa    420
gcgctgattg ctaaagccaa agcatggact ctgaagctgt cgacttatga tcctgaaggc    480
gtcacgtctc gtggttacaa tgacgaagct gcgtttcgtg ttattgcggc tatggcatgg    540
ggttacgatt ggttacatgc ttactttacc gatgaagagc ggcagcaagt tcaaaatgca    600
ttagtgaccc gcctggacga aatcatgcac cacctgaaag tgacggttga cctacttagc    660
aacccgctga acgtcacgg tgttcgttct atttcttcag ctatcatccc aacatgtatc    720
gcgctttatc acgatcaccc gaaagcgggt gagtacatcg catacgcgtt agaatattat    780
gcagtgcact acccaccatg gggcggagaa gatggcggct gggcagaagg tcctgattac    840
tggaatacgc aaacggcttt cctaggtgaa gctttcgacc tattaaaagc gtactgtggc    900
gtagacatgt tcaataaaac gttctacgaa acaccggcg atttcccact atactgtatg    960
cccgttcact ctaagcgtgc gagtttctgt gaccagtcat cgatcggtga tttccctggt   1020
ctgaagctgg cttacaatat caagcattac gcaggtgtta accagaagcc agagtacgtt   1080
tggtattaca atcaactaaa aggtcgtgat acagaagctc acactaaatt ctacaactat   1140
ggctggtggg attttggcta cgacgatctt cgtttcaaca ttctttggga tgcgcctgag   1200
gagcaagcgc cgtcaaatga cccgttgttg aaagtattcc cgattacagg ttgggctgca   1260
ttccacaata agatgactga acgtgataac cacatccata tggtgttcaa gtgctctccg   1320
```

| | |
|---|---|
| tttggttcta tcagtcattc acatggtgac cagaacgcat ttacgctaca tgccttcggt | 1380 |
| gaaactttag cggcgatcac cggctattac ggcggcttcg gcgtagatat gcacacgaaa | 1440 |
| tggcgtcgcc aaacgttctc taaaaacttg cctctatttg gtggtaaagg ccaatatggc | 1500 |
| gagaacaaaa atacaggcta cgaaaaccac caagaccgtt tctgtattga agcgggcggt | 1560 |
| aatatcacag actacgatac tgaatctgat gtgaagatgg tagaaggtga tgcaactgca | 1620 |
| tcttataagt acttcgttcc tgagatcgaa tcttacaagc gtaagatctg gtttgttcaa | 1680 |
| ggcaaagttt ttgtaatgca agacaaggcg acgctttctg aagagaaaga catgacgtgg | 1740 |
| ttgatgcata ccacgtttgc taacgaagtg gcggataagt cattcactgt ccggggtgaa | 1800 |
| gtcgcgcacc tagacgtgaa ctttattaac gaatccgctg gtaatatcgc ttctgttaag | 1860 |
| aacgttgaag gcttcggtga agttgatccg tatgaataca aagagttaga aatccaccgt | 1920 |
| catgttgaag tggaattcaa gccatccaac gagcacaaca tcttaactct tctggttcct | 1980 |
| aataagaacg agggtgagca agttgaagtt tcttataagc tggaaggtaa cgtcttactt | 2040 |
| ctgacagtag atggtgaagc cgtagaaatt gatttgtctt aa | 2082 |

<210> SEQ ID NO 4
<211> LENGTH: 1401
<212> TYPE: DNA
<213> ORGANISM: Vibrio natriegens

<400> SEQUENCE: 4

| | |
|---|---|
| caagtcgagc ggaaacgagt taactgaacc ttcgggggac gttaacggcg tcgagcggcg | 60 |
| gacgggtgag taatgcctag gaaattgccc tgatgtgggg gataaccatt ggaaacgatg | 120 |
| gctaataccg catgatgcct acgggccaaa gaggggggacc ttcgggcctc tcgcgtcagg | 180 |
| atatgcctag gtgggattag ctagttggtg aggtaagggc tcaccaaggc gacgatccct | 240 |
| agctggtctg agaggatgat cagccacact ggaactgaga cacggtccag actcctacgg | 300 |
| gaggcagcag tggggaatat tgcacaatgg gcgcaagcct gatgcagcca tgccgcgtgt | 360 |
| gtgaagaagg ccttcgggtt gtaaagcact ttcagtcgtg aggaaggttt atgcgttaat | 420 |
| agcgtataga tttgacgtta gcgacagaag aagcaccggc taactccgtg ccagcagccg | 480 |
| cggtaatacg gagggtgcga gcgttaatcg gaattactgg gcgtaaagcg catgcaggtg | 540 |
| gtttgttaag tcagatgtga aagcccgggg ctcaacctcg aatagcatt tgaaactggc | 600 |
| agactagagt actgtagagg ggggtagaat ttcaggtgta gcggtgaaat gcgtagagat | 660 |
| ctgaaggaat accggtggcg aaggcggccc cctggacaga tactgacact cagatgcgaa | 720 |
| agcgtgggga gcaaacagga ttagataccc tggtagtcca cgccgtaaac gatgtctact | 780 |
| tggaggttgt ggccttgagc cgtggctttc ggagctaacg cgttaagtag accgcctggg | 840 |
| gagtacggtc gcaagattaa aactcaaatg aattgacggg ggcccgcaca agcggtggag | 900 |
| catgtggttt aattcgatgc aacgcgaaga accttaccta ctcttgacat ccagagaact | 960 |
| ttccagagat ggattggtgc cttcgggaac tctgagacag tgctgcatg gctgtcgtca | 1020 |
| gctcgtgttg tgaaatgttg ggttaagtcc cgcaacgagc gcaacccta tccttgtttg | 1080 |
| ccagcgagta atgtcgggaa ctccagggag actgccggtg ataaaccgga ggaaggtggg | 1140 |
| gacgacgtca agtcatcatg gcccttacga gtagggctac acacgtgcta caatggcgca | 1200 |
| tacagagggc ggccaacttg cgaaagtgag cgaatcccaa aaagtgcgtc gtagtccgga | 1260 |
| ttggagtctg caactcgact ccatgaagtc ggaatcgcta gtaatcgtgg atcagaatgc | 1320 |
| cacggtgaat acgttcccgg gccttgtaca caccgcccgt cacaccatgg gagtgggctg | 1380 |

```
caaaagaagt aggtagttta a                                                    1401

<210> SEQ ID NO 5
<211> LENGTH: 33
<212> TYPE: DNA
<213> ORGANISM: Artificial sequence
<220> FEATURE:
<223> OTHER INFORMATION: synthetic DNA

<400> SEQUENCE: 5
cgcggatcca tgaagcatat tttcttcaaa agc                                         33

<210> SEQ ID NO 6
<211> LENGTH: 23
<212> TYPE: DNA
<213> ORGANISM: Artificial sequence
<220> FEATURE:
<223> OTHER INFORMATION: synthetic DNA

<400> SEQUENCE: 6
cctcgaggcc ttggtactta cca                                                    23
```

ALGINATE LYASE AND APPLICATION THEREOF

TECHNICAL FIELD

The disclosure relates to an alginate lyase and application thereof, and belongs to the technical field of biology.

BACKGROUND

Alginate is a linear polysaccharide formed by polymerization of two sugar moieties of β-D-mannuronate and α-L-guluronate through 1,4 glycosidic bonds. China is the world's largest producer of alginate, with a production volume exceeding 70% of the total output. Alginate oligosaccharide (AOS) is a degradation product of alginate, containing 2-20 sugar moieties and having a small molecular weight. AOS can overcome the limitation that alginate macromolecules cannot pass through various biological barriers in the body, and has a wider range of application. AOS shows more remarkable bioactivity than alginate polysaccharide, such as anticoagulation, blood sugar and lipid reduction, anti-inflammation, antioxidation, anti-tumor and immune regulation, and can also promote growth of beneficial microorganisms such as bifidobacteria.

Alginate lyases belong to the family of polysaccharide lyase (EC 4.2.2), and can be divided into poly β-D-1,4-mannuronate lyase (EC 4.2.2.3) and poly α-L-1,4-guluronate lyase (EC 4.2.2.11) according to different ways of degrading a substrate. Alginate lyases have a wide range of origins, mainly from seaweed plants, marine bacteria, fungi, molluscs, etc. However, the current enzyme preparations have few types and high cost, which limits the application and development of the enzyme.

Alginate lyases are mostly induced enzymes, that is, a substrate sodium alginate must be added to a fermentation medium to induce a wild strain to produce extracellular alginate lyases secreted into the medium, while sodium alginate is not likely to dissolve and has high solution viscosity, which causes certain difficulties in industrial production.

An *Escherichia coli* expression system has the advantages of simple operation and large-scale fermentation and incubation, and is often used in high-level expression of apoenzyme. Alginate lyases reported so far usually exist as an intracellular enzyme in *E. coli*, while there are very few reports of *E. coli* engineered strains that can secrete recombinant alginate lyases extracellularly. If the enzyme can be secreted extracellularly (in the medium), there are many advantages over localization in the cytoplasm, such as, simplifying downstream protein processing, promoting protein folding and stability, and improving protein solubility and bioactivity.

SUMMARY

The disclosure screened a fast-growing wild strain from sea mud, which was identified and named as *Vibrio natriegens* SK42.001, and was deposited in the China Center for Type Culture Collection (CCTCC) on Jan. 5, 2017, with the deposit number of CCTCC M2017011.

The disclosure also provides a new alginate lyase Aly01, the amino acid sequence of which is shown in SEQ ID NO: 1. The nucleotide sequence of a gene encoding the alginate lyase may be as shown in SEQ ID NO: 2, wherein 1-78 bp encode a signal peptide.

The disclosure also provides a method for producing the new alginate lyase Aly01 by using the *V. natriegens* SK42.001, including the following steps:

(1) seed culture: in a seed medium containing 5 of sodium alginate, 5 of $(NH_4)_2SO_4$, 30 of NaCl, 1 of $MgSO_4 \cdot 7H_2O$, 2 of $K_2HPO_4$, and 0.01 of $FeSO_4 \cdot 7H_2O$, inoculating *V. natriegens* SK42.001 into the seed medium and incubating at 28° C. and 200 rpm on a shaker for 12 h;

(2) fermentation culture: in a fermentation medium containing 8 of sodium alginate, 5 of $NH_4Cl$, 30 of NaCl, 1 of $MgSO_4 \cdot 7H_2O$, 2 of $K_2HPO_4$, and 0.01 of $FeSO_4 \cdot 7H_2O$, and under fermentation conditions of an inoculation amount of 5%, a temperature of 28° C., a rotation speed of 200 rpm, and a fermentation time of 36 h, obtaining a fermentation broth containing an alginate lyase; and (3) purification: centrifuging the fermentation broth to remove thallus to obtain an alginate lyase crude enzyme; performing separation and precipitation of target protein by 20%-80% ammonium sulfate, buffer dialysis, DEAE-FF 16/10 ion exchange chromatography, and Superdex 75 gel filtration chromatography; and finally, freeze-drying a purified Aly01 pure enzyme liquid to obtain enzyme powder.

The disclosure also provides a method for specifically producing alginate oligosaccharide trisaccharide using the alginate lyase Aly01, including: using sodium alginate as a substrate and NaCl as an enzyme stabilizer, degrading sodium alginate in a buffer system of pH 6.5-9 to synthesize the alginate oligosaccharide trisaccharide. The amount of the NaCl stabilizer is preferably 100 mM or more. The method is preferably performed at 25-40° C., especially 35° C.

The disclosure also provides an *E. coli* engineered strain with high production of an extracellular recombinant alginate lyase, wherein the strain uses *E. coli* as a host to express a gene encoding the alginate lyase derived from *V. natriegens* SK42.001.

In one embodiment of the disclosure, the *E. coli* is *E. coli* BL21.

In one embodiment of the disclosure, pET-28a(+) is used as an expression vector to construct a recombinant expression vector.

The disclosure also provides a method for constructing the *E. coli* engineered strain, including: using a upstream primer CGCGGATCCATGAAGCATATTTTCTT-CAAAAGC (BamH I), and a downstream primer CCTCGAGGCCTTGGTACTTACCA (Xho I), performing PCR amplification on the gene encoding the alginate lyase shown in SEQ ID NO: 2; ligating the gene fragment encoding the alginate lyase to a vector pET-28a(+); and constructing and transforming an expression vector pET28a-aly into *E. coli* BL21 competent cells to construct the *E. coli* engineered strain *E. coli* BL21-aly01 that produces the alginate lyase.

The disclosure also provides a method for producing an alginate lyase using the *E. coli* engineered strain, including: inoculating a seed solution into an LB medium, and after a period of incubation, adding IPTG to induce expression of the alginate lyase.

In one embodiment of the disclosure, the seed solution is inoculated into an LB medium at an inoculum amount of 2-5%, and incubated at 35-37° C. and 180-200 rpm until $OD_{600}$ is 0.6-0.8, and 0.5-1 mM IPTG is added to induce incubation at 15-18° C. and 180-200 rpm for 45-48 h.

In one embodiment of the disclosure, the fermentation broth is centrifuged to remove thallus to obtain a recombinant alginate lyase crude enzyme, which is subjected to nickel column affinity chromatography and dialyzed to obtain an Aly01 pure enzyme liquid, and the pure enzyme liquid is freeze-dried to obtain enzyme powder.

In one embodiment of the disclosure, a single colony of the E. coli engineered strain is picked into an LB medium containing kanamycin, and incubated to obtain the seed solution.

The expression vector pET28a-aly in the E. coli engineered strain E. coli BL21-aly01 constructed in the disclosure includes the full length of the gene encoding the extracellular alginate lyase derived from V. natriegens SK42.001, and includes a signal peptide, a carbohydrate binding domain and a catalytic activity domain. The engineered host strain E. coli BL21 can recognize a signal peptide derived from V. natriegens SK42.001, and further can fermentatively produce the alginate lyase and secrete the alginate lyase extracellularly. Most of E. coli engineered strains producing the alginate lyase in the prior art produce intracellular recombinase, and the signal peptide part needs to be cut off or only an expression vector containing the catalytic activity domain is constructed.

Beneficial Effects of the Disclosure:

1. The V. natriegens SK42.001 provided by the disclosure has the following characteristics:
   (1) The V. natriegens has high growth rate, which is nearly twice that of a reference strain E. coli BL21. In an LB medium with an NaCl concentration of 3%, the culture generation time of V. natriegens SK42.001 is 16.2 min, while that of E. coli BL21 is 31.4 min. A single colony of SK42.001 grows 5 h after streaking on an LB plate, while E. coli BL21 takes 10 h.
   (2) The V. natriegens contains its own natural plasmids, the size of which is about 3000 bp. The V. natriegens can express exogenous genes, and has development value and application potential as a new model organism.
   (3) The V. natriegens can hydrolyze gelatin, and can use starch and maltose.
   (4) The V. natriegens aerobically grows.
   (5) The V. natriegens contains the gene (SEQ ID NO: 2) encoding the alginate lyase, and contains the gene (SEQ ID NO: 3) encoding an oligo-alginate lyase.
   (6) Some protein coding genes contained are different from other V. natriegens strains, such as a xanthan lyase, and pilin TadC, TadE and CpaB.

2. The alginate lyase obtained in the disclosure has high degradation activity, and the enzyme activity reaches 65 U/mg; the alginate lyase is stable in nature, and the enzyme activity remains 98% or higher of the initial enzyme activity after storage at 4° C. for 18 months; and the alginate lyase has high product specificity and can specifically produce alginate oligosaccharide trisaccharide. The alginate lyase obtained by the disclosure has stable properties and high product specificity, which are not seen in the reported alginate lyase related literature, and has important industrial application value and scientific research value.

3. The engineered strain constructed by the disclosure can produce the alginate lyase secreted extracellularly in a conventional LB medium without adding an induction substrate sodium alginate, so the downstream processing technology of protein is simplified, and the disclosure has great industrial application potential.

Deposit of Biological Material

V. natriegens SK42.001 was deposited in the China Center for Type Culture Collection (CCTCC) on Jan. 5, 2017, the deposit address is Wuhan University, Wuhan, China, and the deposit number is CCTCC NO: M2017011.

DETAILED DESCRIPTION

Media:

Liquid medium and screening liquid medium containing: 5 g of sodium alginate, 5 g of $(NH_4)_2SO_4$, 30 g of NaCl, 1 g of $MgSO_4 \cdot 7H_2O$, 2 g of $K_2HPO_4$, 0.01 g of $FeSO_4 \cdot 7H_2O$, and 1000 mL of distilled water, with a pH of 7.2.

Plate medium containing: 5 g of sodium alginate, 5 g of $(NH_4)_2SO_4$, 30 g of NaCl, 1 g of $MgSO_4 \cdot 7H_2O$, 2 g of $K_2HPO_4$, 0.01 g of $FeSO_4 \cdot 7H_2O$, 1000 mL of distilled water with a pH of 7.2, and 20 g of agar.

Enzyme activity measurement: 1 mL of an enzyme reaction solution (50 mM PB buffer with a pH of 7.0) contains 5 mg of sodium alginate, 300 mM NaCl, and 0.84 µg of alginate lyase or fermentation supernatant, and reacts at 35° C. for 30 min, and the supernatant is taken for detecting the enzyme activity by a DNS method. Definition of enzyme activity: The amount of enzyme required to produce 1 µmol of reducing sugar per minute.

Example 1 Production Method of Alginate Lyase Aly01

A: Screening Method of V. natriegens (1) Sea mud was sampled from the vicinity of a kelp breeding plant in Rongcheng, Shandong, and 1 g of the sample was dispersed evenly in 50 mL of sterile water.

(2) 1 mL of supernatant was inoculated in 50 mL of screening liquid medium and incubated at 28° C. and 200 rpm for 2 days. The culture was diluted by $10^{-6}$, spread on a screening plate medium and incubated at 28° C. for 2 days, and single colonies of different morphology were picked and streaked on the plate several times to obtain a pure culture.

(3) The single colonies of different morphology were picked, inoculated into a liquid medium, and incubated at 28° C. and 200 rpm for 2 days. The supernatant was taken to measure the enzyme activity of strains, and the strain with higher enzyme activity was selected and commissioned to be preserved by the China Center for Type Culture Collection, and the morphological characteristics, physiological-biochemical characteristics and 16S rDNA sequence of the strain were analyzed.

B: Identification of *V. natriegens*

(1) Plate Colony Morphology

The plate colony morphology of *V. natriegens* SK42.001 was as follows: A colony grew rapidly after streaking on a plate medium. A single colony came out after 24 h of incubation at 28° C. The colony was round and convex, milky white, moist and slightly sticky, with a smooth surface, flat edges, and a diameter of 0.6-0.8 cm.

(2) Thallus Characteristics Under Electron Microscope

The thallus characteristics of *V. natriegens* SK42.001 under an electron microscope were as follows: A thallus is short, obtuse at both ends, curved into an arc, with a size of 0.6-0.8 μm×1.2-1.4 μm.

(3) Physiological-Biochemical Characteristics

Physiological-biochemical characteristics of *V. natriegens* SK42.001: *V. natriegens* was Gram stain-negative; aerobically grows; was negative in an indole reaction; could hydrolyze gelatin and weakly hydrolyze esculin; could not hydrolyze arginine, urea and s-galactoside; could use glucose, sucrose, starch, arabinose and mannose; and could not use fructose, maltose, inulin, xylose, galactose, sorbose and xylitol. In particular, the *V. natriegens* provided by the disclosure could hydrolyze gelatin and could use starch and maltose.

The 16S rDNA of *V. natriegens* SK42.001 (a nucleotide sequence was shown in SEQ ID NO: 4) was compared with data in the NCBI database, and the result showed that *V. natriegens* SK42.001 has extremely high homology with *V. natriegens*.

TABLE 1

Physiological-biochemical characteristics of strain SK42.001-enzyme activity and carbon source oxidation

| | Reaction substrate | and reaction enzyme | Test result |
|---|---|---|---|
| ONPG | O-nitrobenzene-galactoside | β-galactosidase | − |
| ADH | Arginine | Arginine dihydrolase | − |
| LDC | Lysine | Lysine decarboxylase | − |
| ODC | Ornithine | Ornithase decarboxylation | − |
| CIT | Sodium citrate | Utilization of citric acid | + |
| H2S | Sodium thiosulfate | Generation of H2S | − |
| URE | Urea | Urease | − |
| TDA | Tryptophan | Tryptophan desaminase | + |
| IND | Tryptophan | Production of indole | − |
| VP | Pyruvate | Production of acetylmethyl carbinol by 3-hydroxybutanone | + |
| GEL | Kohn gelatin | Gelatinase | + |
| GLU | Glucose | Fermentation/oxidation (4) | + |
| MAN | Mannitol | Fermentation/oxidation (4) | + |
| INO | Inositol | Fermentation/oxidation (4) | − |
| SOR | Sorbitol | Fermentation/oxidation (4) | − |

TABLE 1-continued

Physiological-biochemical characteristics of strain SK42.001-enzyme activity and carbon source oxidation

| | Reaction substrate | and reaction enzyme | Test result |
|---|---|---|---|
| RHA | Rhamnose | Fermentation/oxidation (4) | + |
| SAC | Sucrose | Fermentation/oxidation (4) | + |
| MEL | Melibiose | Fermentation/oxidation (4) | − |
| AMY | Amygdalin | Fermentation/oxidation (4) | + |
| ARA | Arabinose | Fermentation/oxidation (4) | + |

+: positive reaction;
−: negative reaction

TABLE 2

Physiological-biochemical characteristics of strain SK42.001-production of acid using carbon source

| Reagent strip corresponding tube/substrate | Test result |
|---|---|
| 0 control | − |
| 1 glycerin | − |
| 2 erythritol | − |
| 3 D-arabinose | + |
| 4 L-arabinose | + |
| 5 ribose | − |
| 6 D-xylose | − |
| 7 L-xylose | − |
| 8 adonitol | − |
| 9 β-methyl-D-xyloside | − |
| 10 galactose | − |
| 11 glucose | + |
| 12 fructose | − |
| 13 mannose | + |
| 14 sorbose | − |
| 15 rhamnose | + |
| 16 dulcitol | − |
| 17 inositol | − |
| 18 mannitol | + |
| 19 sorbitol | − |
| 20 α-methyl-D-mannoside | − |
| 21 α-methyl-D-glucoside | − |
| 22 N-acetyl-glucosamine | − |
| 23 amygdalin | + |
| 24 arbutin | − |
| 25 esculin | W |
| 26 salicin | − |
| 27 cellobiose | − |
| 28 maltose | − |
| 29 lactose | − |
| 30 melibiose | + |
| 31 sucrose | + |
| 32 trehalose | − |
| 33 inulin | − |
| 34 melezitose | − |
| 35 raffinose | − |
| 36 starch | + |
| 37 glycogen | − |
| 38 xylitol | − |
| 39 geraniol | − |
| 40 D-turanose | − |
| 41 D-lyxose | − |
| 42 D-tagatose | − |
| 43 D-fucose | − |
| 44 L-fucose | − |

TABLE 2-continued

Physiological-biochemical characteristics of
strain SK42.001-production of acid using
carbon source

| Reagent strip corresponding tube/substrate | Test result |
|---|---|
| 45 D-arabitol | − |
| 46 L-arabitol | − |
| 47 gluconate | − |
| 48 2-keto-gluconate | − |
| 49 5-keto-gluconate | + |

+: positive reaction;
−: negative reaction;
w: weakly positive reaction

Example 2 Feasibility of *V. natriegens* as New Model Organism (1) Measurement of Growth Rate In an LB3 liquid medium (LB medium with a NaCl concentration of 3%), the culture generation time of *V. natriegens* was 16.2 min, while that of the reference strain *E. coli* BL21 was 31.4 min. A single colony of SK42.001 grew 5 h after streaking on an LB plate, while *E. coli* BL21 takes 10 h. Therefore, the SK42.001 had a high growth rate, which was nearly twice that of *E. coli*.

(2) Feasibility of SK42.001 to Express Exogenous Genes

Figure 1:
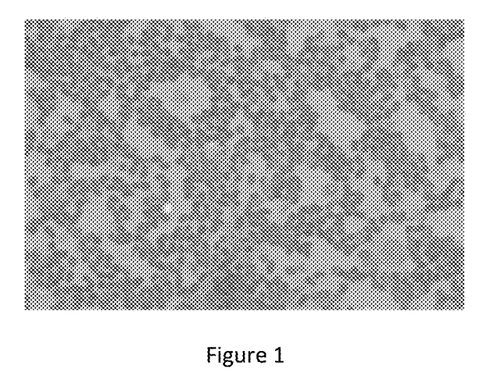
FIG. 1 shows a photo of the morphology of the strain SK42.001 under a microscope (1000×).
Figure 2:
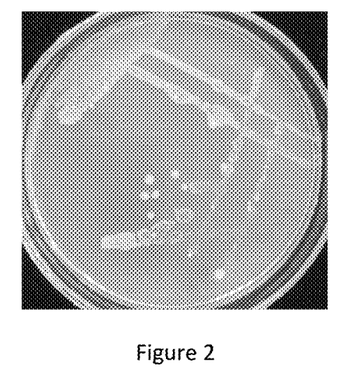
FIG. 2 shows the plate colony morphology of the strain SK42.001.
Figure 3:
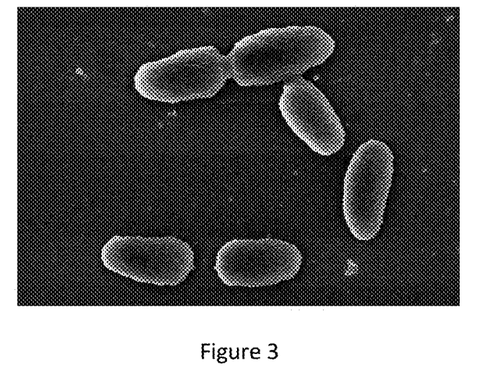
FIG. 3 show a photo of the cell morphology of the strain SK42.001 under an electron microscope (20000×).
Figure 4:
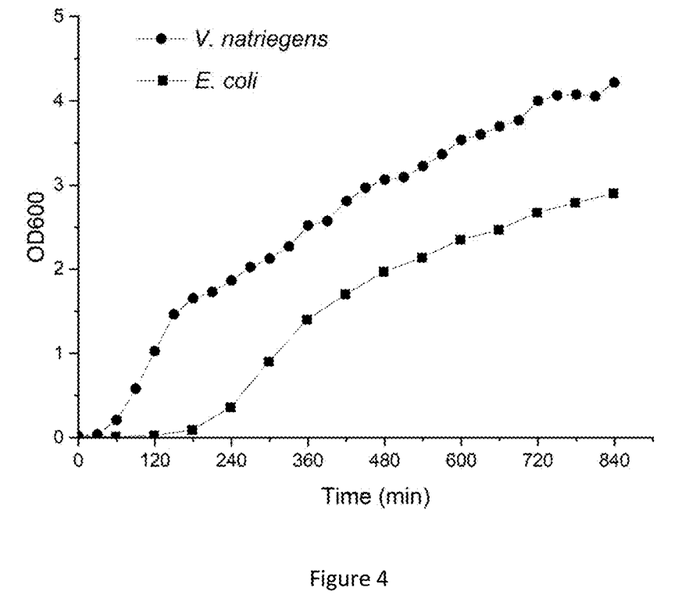
FIG. 4 shows the growth curves of V. natriegens SK42.001 and E. coli BL21.
Figure 5:
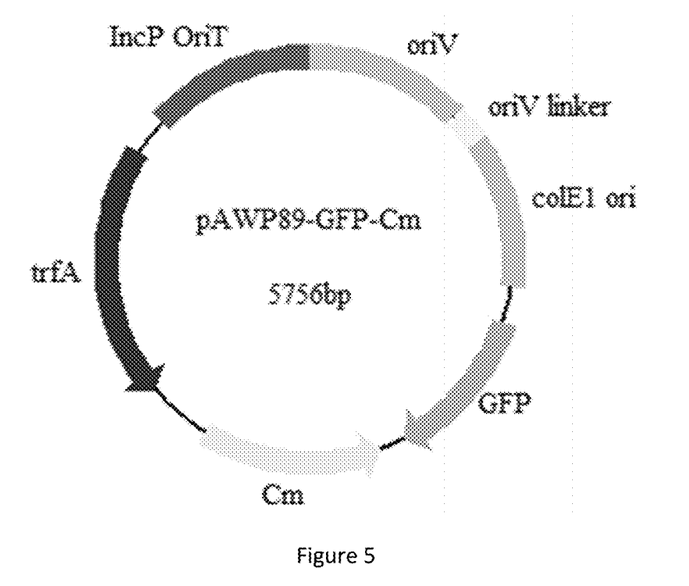
FIG. 5 shows the recombinant plasmid pAWP89-GFP-Cm.
Figure 6:
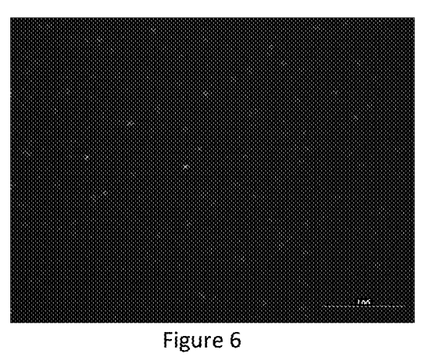
FIG. 6 shows expression of GFP by SK42.001 conjugating a recombinant strain.

A broad host range plasmid pAWP89 was selected to construct a recombinant plasmid pAWP89-GFP-Cm containing green fluorescent protein (GFP) reporter gene and chloramphenicol (Cm) resistance gene selection markers (FIG. 5). Using a pRK2013 helper plasmid, the pAWP89-GFP-Cm was introduced into SK42.001 through triparental conjugation, and the conjugated SK42.001 recombinant strain emits green fluorescence under blue light excitation (FIG. 6). Therefore, the SK42.001 could be used as a host strain to express exogenous target genes.

The above result indicated that the *V. natriegens* SK42.001 strain had development value and application potential as a new model organism.

Example 3 Gene Characteristics of *V. natriegens*

*V. natriegens* SK42.001 was 100% consistent with *V. natriegens* CCUG16374, which was one of strains used by Daniel Gibson's research group of Synthetic Genomics in California. *V. natriegens* SK42.001 was 99% consistent with the strain *V. natriegens* ATCC14048 (or DSM759) shared by the George Church group of Harvard University and Gibson. However, the whole genomes of *V. natriegens* SK42.001 and *V. natriegens* CCUG16374 were not exactly same.

(1) SK42.001 contained some coding genes that CCUG16374 did not have, for example:
   I: SK42.001 contained a gene (SEQ ID NO: 2) encoding the alginate lyase.
   II: SK42.001 contained a gene (SEQ ID NO: 3) encoding the oligo-alginate lyase.

(2) SK42.001 and CCUG16374 had some protein coding genes that were different, for example:
   I: A gene of SK42.001 encoding a xanthan lyase and a gene of CCUG16374 encoding the xanthan lyase had a similarity of 98%, and had 69 different bases and 18 Gaps.
   II: Some pilin related to the formation of bacterial pili were quite different.
   a: The similarity of pili assembly protein TadC was 77%, with 201 different bases and 6 Gaps.
   b: The similarity of pili synthetic protein TadE was 82%, with 79 different bases and 6 Gaps.
   c: The similarity of pili Flp type assembly protein CpaB was 79%, with 154 different bases and 10 Gaps.

(3) *V. natriegens* SK42.001 had its own natural plasmids, but other *V. natriegens* strains that had been reported did not have natural plasmids.

Figure 7:
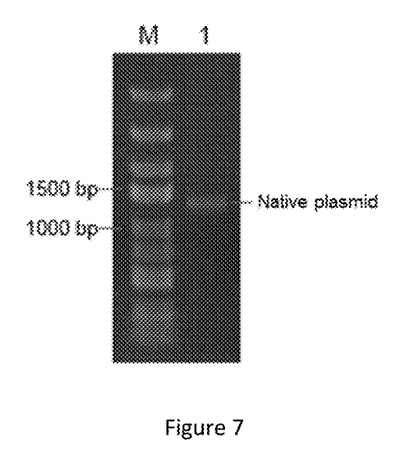
FIG. 7 shows a natural plasmid extracted from a SK42.001 wild strain, wherein M is a DL5000 marker; 1 is the natural plasmid extracted from the SK42.001 wild strain; the plasmid in the photo shows a supercoiled structure; and the band is at ½ of the actual size.

A single colony of *V. natriegens* SK42.001 was picked and inoculated into 50 mL of liquid medium, and incubated at 28° C. and 200 rpm for 2 days. The plasmids of a SK42.001 wild strain were extracted by using a SanPrep column plasmid DNA small volume extraction kit, and detected by 1% agarose gel electrophoresis (FIG. 7). It was found that the SK42.001 wild strain contains its own natural plasmids, which were about 3000 bp in size. The plasmid in the figure shows a supercoiled structure, and the band was at ½ of the actual size.

Example 4 Preparation of Alginate Lyase

The *V. natriegens* SK42.001 screened in Example 1 was subjected to three-stage culture and production including slant culture, seed culture and fermentation culture. The components of media were counted in g/L:
   a: Slant culture: A slant medium contains 5 of sodium alginate, 5 of $(NH_4)_2SO_4$, 30 of NaCl, 1 of $MgSO_4.7H_2O$, 2 of $K_2HPO_4$, 0.01 of $FeSO_4.7H_2O$, and 15-20 of agar, had a natural pH, was prepared with deionized water, and was sterilized at 121° C. for 20 min. Slant culture conditions were a culture temperature 25-30° C. and a culture time 1-3 days.
   b: Seed culture: A seed medium contained 5 of sodium alginate, 5 of $(NH_4)_2SO_4$, 30 of NaCl, 1 of $MgSO_4.7H_2O$, 2 of $K_2HPO_4$, and 0.01 of $FeSO_4.7H_2O$, had a natural pH, was prepared with deionized water, and was sterilized at 121° C. for 20 min. Seed culture conditions were 28° C. and 200 rpm on a shaking table for 12 h.
   c: Fermentation culture: A fermentation medium contained 8 of sodium alginate, 5 of $NH_4Cl$, 30 of NaCl, 1 of $MgSO_4.7H_2O$, 2 of $K_2HPO_4$, and 0.01 of $FeSO_4.7H_2O$, had a natural pH, was prepared with deionized water, and was sterilized at 121° C. for 20 min. Fermentation conditions were an inoculum amount of 5%, a temperature of 28° C., a rotation speed of 200 rpm, and fermentation on a shaker for 36 h to obtain a fermentation broth containing the alginate lyase. The enzyme activity of the fermentation broth measured was 4.5 U/mL. The enzyme activity of fermentation supernatant was detected by the DNS method by using 50 mM PB buffer with a pH of 7.0 as the buffer system, sodium alginate as a substrate, and 300 mM NaCl as a stabilizer at 35° C. for 30 min. Definition of enzyme activity: The amount of enzyme required to produce 1 μmol of reducing sugar per minute.

Figure 8:
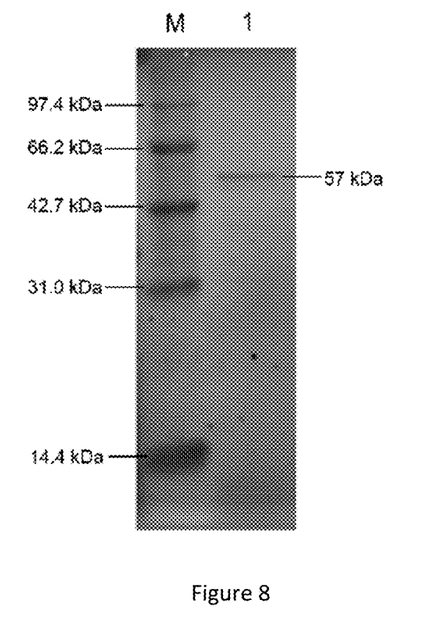
FIG. 8 shows an SDS-PAGE analysis of the purified Aly01 enzyme.

The fermentation broth was centrifuged to remove bacteria to obtain an alginate lyase crude enzyme. After separation and precipitation of target protein by 20%-80% ammonium sulfate, buffer dialysis, DEAE-FF 16/10 ion exchange chromatography, and Superdex 75 gel filtration chromatography were performed, finally, a purified Aly01 pure enzyme liquid (FIG. 8) was freeze-dried to obtain enzyme powder. The purification multiple was 7.63-8.17 times, and the final yield was 56.5-61.3%.

Example 5 Sequence Alignment

After amino acid sequencing of the enzyme, a primer was designed to amplify the gene encoding the alginate lyase from the *V. natriegens* SK42.001 genome. The nucleotide sequence of the gene was shown in SEQ ID NO: 2. The DNA sequence BLAST result was as follows: the alginate lyase provided by the disclosure had the closest DNA sequence homology to the alginate lyase derived from *Vibrio alginolyticus* FDAARGOS, but the similarity was only 85%, with 231 different bases and 8 Gaps.

The amino acid sequence BLAST result was as follows: the alginate lyase provided by the disclosure had the closest amino acid sequence homology to an alginate lyase derived from a *Vibrio* genus in the NCBI database, with a similarity of 93%, 39 different amino acids, and 0 Gap.

Figure 9:
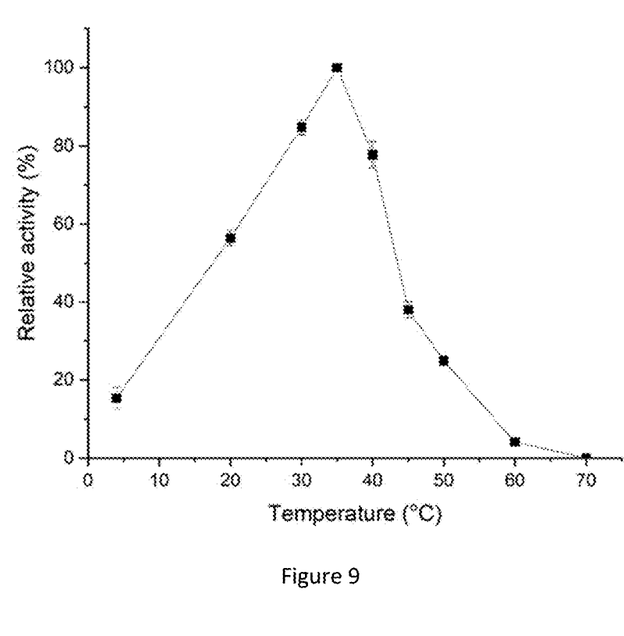
FIG. 9 shows the influence of temperature on the Aly01.

Example 6 Study on Enzymatic Properties of Alginate Lyase (1) Influence of temperature on enzyme activity: 1 mL of an enzyme reaction solution (50 mM PB buffer with a pH of 7.0) contained 5 mg of sodium alginate, 300 mM NaCl and 0.84 µg of alginate lyase. The enzyme reaction solution was placed in a water bath at 4° C., 20° C., 30° C., 35° C., 40° C., 50° C., 60° C. and 70° C. for 30 min respectively, and the enzyme activity of the alginate lyase at each temperature was measured. As shown in FIG. 9, the optimal reaction temperature was 35° C.

Figure 10:
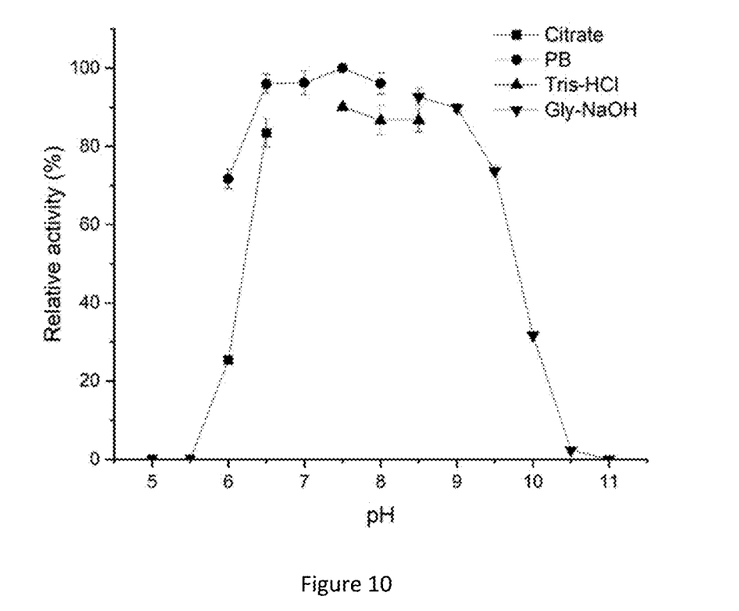
FIG. 10 shows the influence of pH on the Aly01.

(2) Influence of pH on enzyme activity: 1 mL of enzyme reaction solution contained 5 mg of sodium alginate, 300 mM of NaCl, and 0.84 µg of alginate lyase. Buffers (50 mM) with different pH values were used, including acetic acid-sodium acetate buffers (pH 3.5, 4.0, 4.5, 5.0), citrate buffers (pH 5.0, 5.5, 6.0, 6.5), phosphate buffers (pH 6.0, 6.5, 7.0, 7.5, 8.0), Tris-hydrochloric acid buffers (pH 7.5, 8.0, 8.5), and glycine-NaOH buffers (pH 8.5, 9.0, 9.5, 10, 10.5, 11). The enzyme reaction solution was reacted at 35° C. for 30 min to measure the enzyme activity at each pH. As shown in FIG. 10, the alginate lyase showed high pH adaptability and could maintain 90% or higher of activity in a pH range of 6.5-9.

Figure 11:
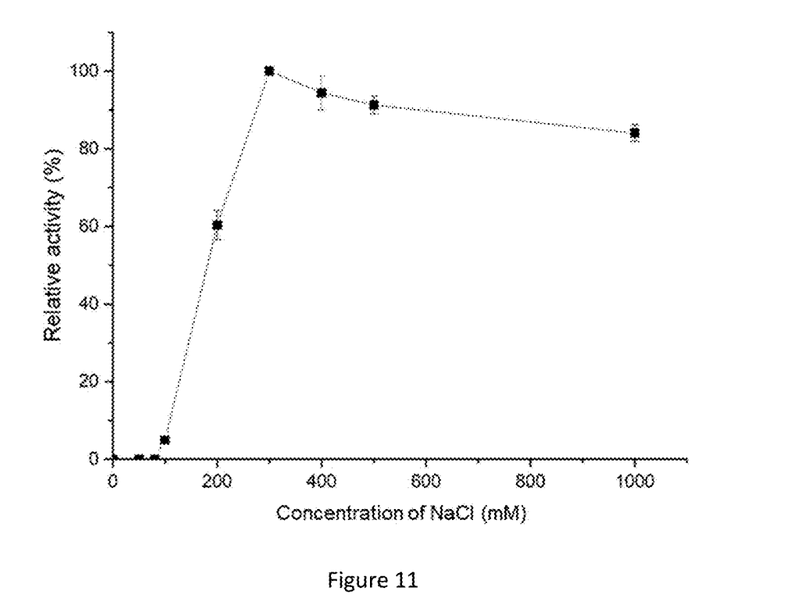
FIG. 11 shows the influence of NaCl on the Aly01.

(3) Influence of NaCl on enzyme activity: 1 mL of enzyme reaction solution (50 mM PB buffer with a pH of 7.0) contained 5 mg of sodium alginate and 0.84 µg of alginate lyase. NaCl with a final concentration of 0, 50, 80, 100, 200, 250, 300, 400, 500 and 1000 mM was added respectively. The enzyme reaction solution was reacted at 35° C. for 30 min to measure the enzyme activity at different concentration of NaCl. The alginate lyase had high dependence on NaCl, and had obvious degradation activity only when the concentration of NaCl was greater than or equal to 100 mM (FIG. 11).

(4) Product Specificity:

1 mL of enzyme reaction system contained 300 mM NaCl, 0.84 µg of alginate lyase and 10 mg of sodium alginate, was constant volume with 50 mM PB buffer with a pH of 7.0, and was reacted at 35° C. for 12 h. The reaction solution was detected by thin layer chromatography (TLC). The specific method was: a silica gel plate of a certain size was made; a line parallel to the bottom side was drawn with a pencil on the bottom side, and several equidistant points were marked on the line with a pencil; 1 µL of disaccharide (DP2) (1 mg/mL), 1 µL of trisaccharide (DP3) standard (1 mg/mL), 1 µL of reaction solution, and 1 µL of sodium alginate substrate (10 mg/mL) were respectively placed on the marked points; the silica gel plate was placed ventilated to dry completely; and then put in a saturate tank containing a developing agent to start chromatography until the liquid reaches the top of the silica gel plate; and after the chromatography, the silica gel plate was completely dried with a blower, then placed in a color developing solution for 15 s, dried in air, and baked in an oven at 120° C. until the color develops.

Figure 12:
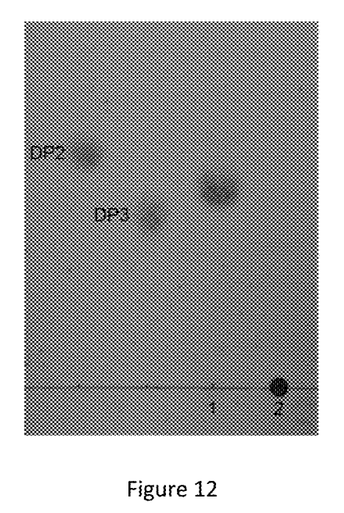
FIG. 12 shows analysis of products of sodium alginate degraded by the Aly01, wherein DP2 is polydimannuronate; DP3 is polytriguluronate; 1 is a 4 h reaction solution of the Aly01 enzyme; and 2 is a solution of the substrate sodium alginate.
Figure 13:
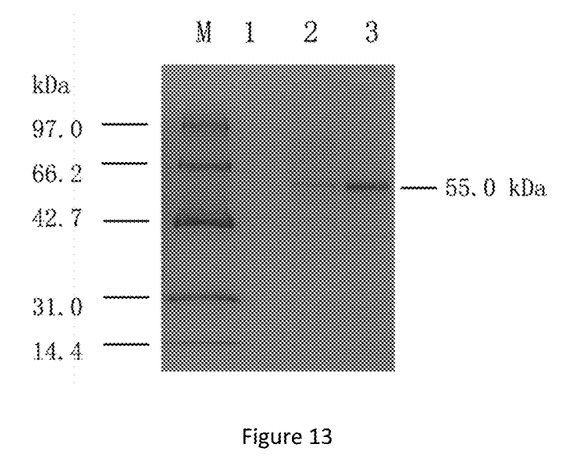
FIG. 13 is an SDS-PAGE analysis chart of the purified extracellular recombinant alginate lyase, wherein M is a molecular weight standard; 1 is a crude enzyme before induction; 2 is the crude enzyme after induction; and 3 is a purified enzyme liquid.

Product analysis: As shown in FIG. 12, when the alginate lyase provided by the disclosure enzymatically degrades the substrate sodium alginate, the degradation rate of the sodium alginate was 100%, and almost all of the sodium alginate was degraded into trisaccharide. The oligosaccharide degraded by the alginate lyase could generate unsaturated double bonds, and compared with the saturated trisaccharide standard, the molecular weight had a difference of the molecular weight of water. Alginate lyases that could specifically degrade the substrate sodium alginate to produce specific alginate oligosaccharide (for example trisaccharide) had not been reported yet.

Example 7

(1) Construction of *E. coli* Engineered Strain *E. coli* BL21-Aly01

The sequence of a gene encoding alginate lyase in the *V. natriegens* SK42.001 genome was shown in SEQ ID NO: 2 (wherein 1-78 bp encode a signal peptide). Using the genome DNA of *V. natriegens* SK42.001 as a template, and using a upstream primer: CGCGGATCCATGAAGCATAT-TTTCTTCAAAAGC (BamH 1), a downstream primer: CCTCGAGGCCTTGGTACTTACCA (Xho 1), PCR amplification was performed on the gene encoding the alginate lyase; the gene fragment encoding the alginate lyase was ligated to a vector pET-28a(+); and an expression vector pET28a-aly was constructed and transformed into *E. coli* BL21 competent cells to construct the *E. coli* engineered strain *E. coli* BL21-aly01 that produces the alginate lyase.

(2) Extracellular Production Method of Recombinant Alginate Lyase

Seed solution culture: A single colony of *E. coli* engineered strain *E. coli* BL21-aly01 was picked into 5 mL of an LB medium containing 50 µg/mL kanamycin, and incubated at 37° C. and 200 rpm on a shaker overnight.

Fermentation induction: The above seed solution was inoculated into 200 mL of LB medium at an inoculum amount of 2%, and incubated on a shaker at 37° C. and 200 rpm until $OD_{600}$ was 0.6-0.8, and 1 mM IPTG was added to induce incubation at 18° C. and 200 rpm for 48 h. The fermentation supernatant was collected by centrifugation as a crude enzyme. After measurement, the enzyme activity of the crude enzyme was 4.5 U/mL.

The fermentation broth was centrifuged to remove bacteria to obtain an alginate lyase crude enzyme, which was purified by ÄKTA nickel column affinity chromatography. After overnight dialysis in 50 mM phosphate buffer with a pH of 7.0, an Aly01 pure enzyme liquid was obtained and freeze-dried to obtain enzyme powder. The purification multiple was 2.62-3.17 times, and the final yield was 65.3-75.9%.

The expression vector pET28a-aly in the *E. coli* engineered strain *E. coli* BL21-aly01 constructed contained the full length of the gene encoding the extracellular alginate lyase derived from *V. natriegens* SK42.001, and included a signal peptide, a carbohydrate binding domain and a catalytic activity domain. The engineered host strain *E. coli* BL21 could recognize a signal peptide derived from *V. natriegens* SK42.001, and further could fermentatively produce the alginate lyase and secrete the alginate lyase extracellularly. Most of *E. coli* engineered strains producing the alginate lyase in the prior art produce intracellular recombinase, and the signal peptide part needed to be cut off or only an expression vector containing the catalytic activity domain was constructed.

Although the disclosure has been disclosed as above in preferred examples, it is not intended to limit the disclosure. Anyone familiar with the technology can make various variations and modifications without departing from the spirit and scope of the disclosure. Therefore, the protection scope of the disclosure should be defined by the claims.

What is claimed is:

1. A recombinant cell, wherein the recombinant cell expresses alginate lyase from *Vibrio natriegens* SK42.001, wherein the amino acid sequence of the alginate lyase is set forth in SEQ ID NO: 1.

2. The recombinant cell of claim 1, wherein the recombinant cell is an *Escherichia coli* cell.

3. The recombinant cell of claim 2, wherein the recombinant cell is *Escherichia coli*-BL21.

4. The recombinant cell of claim 3, comprising a recombinant expression vector wherein the expression vector is pET-28a(+).

5. The recombinant cell of claim 1, wherein the recombinant cell is *Escherichia coli* BL21 comprising pET-28a(+) as an expression vector and wherein the cell expresses a gene with the nucleotide sequence set forth in SEQ ID NO: 2 encoding the alginate lyase.

6. A method for producing the alginate lyase of claim 2, comprising inoculating a seed solution of the recombinant cell of claim 2 into a medium, and after a period of incubation, adding IPTG to induce expression of the alginate lyase.

7. The method of claim 6, wherein the seed solution is inoculated into an LB medium at an inoculum amount of 2-5%, and incubated at 35-370 C and 180-200 rpm until $OD_{600}$ is 0.6-0.8, and 0.5-1 mM IPTG is added to induce incubation at 15-180 C and 180-200 rpm for 45-48 h to obtain a fermentation broth.

8. The method of claim 7, wherein the fermentation broth is centrifuged to remove thallus to obtain a crude enzyme preparation of the alginate lyase, wherein the crude enzyme preparation is subjected to nickel column affinity chromatography and dialysis to obtain a pure enzyme liquid, and wherein the pure enzyme liquid is freeze-dried to obtain an enzyme powder.

9. The method of claim 6, wherein a single colony of the recombinant cell is picked into an LB medium containing kanamycin, and incubated to obtain a seed solution.

10. A method for producing the alginate lyase of claim 5, lyase, comprising inoculating a seed solution of the recombinant cell of claim 5 into a medium, and after a period of incubation, adding IPTG to induce expression of the alginate lyase.

11. The method of claim 10, wherein the seed solution is inoculated into an LB medium at an inoculum amount of 2-5%, and incubated at 35-370 C and 180-200 rpm until $OD_{600}$ is 0.6-0.8, and 0.5-1 mM IPTG is added to induce incubation at 15-180 C and 180-200 rpm for 45-48 h to obtain a fermentation broth.

12. The method of claim 11, wherein the fermentation broth is centrifuged to remove thallus to obtain a crude enzyme preparation of the alginate lyase, wherein the crude enzyme preparation is subjected to nickel column affinity chromatography and dialyzed to obtain a pure enzyme liquid, and wherein the pure enzyme liquid is freeze-dried to obtain enzyme powder.

13. The method of claim 10, wherein a single colony of the recombinant cell is picked into an LB medium containing kanamycin, and incubated to obtain a seed solution.

* * * * *